United States Patent [19]
Schaible et al.

[11] Patent Number: 5,755,223
[45] Date of Patent: May 26, 1998

[54] DELIVERY DEVICE FOR A RESPIRATOR

[75] Inventors: Bernhard Schaible; Thomas Leyer, both of Lübeck; Siegfried Kiske, Krummesse, all of Germany

[73] Assignee: Drägerwerk AG, Lübeck, Germany

[21] Appl. No.: 795,482

[22] Filed: Feb. 11, 1997

[30] Foreign Application Priority Data

Apr. 10, 1996 [DE] Germany .................. 196 14 225.3

[51] Int. Cl.⁶ .................. A62B 7/00; A62B 9/02; A61M 16/00; A61M 15/00
[52] U.S. Cl. .................. 128/205.18; 128/205.24; 128/204.18; 128/204.21; 128/203.12
[58] Field of Search .................. 128/205.18, 205.24, 128/204.18, 204.21, 203.12

[56] References Cited

U.S. PATENT DOCUMENTS

| | | | |
|---|---|---|---|
| 3,951,137 | 4/1976 | Conkle et al. | 128/205.18 |
| 5,645,055 | 7/1997 | Danon | 128/204.25 |
| 5,662,100 | 9/1997 | Fox et al. | 128/205.24 |
| 5,666,947 | 9/1997 | McKay | 128/200.21 |
| 5,673,658 | 10/1997 | Heide et al. | 128/203.15 |
| 5,673,689 | 10/1997 | Power | 128/205.18 |

FOREIGN PATENT DOCUMENTS 38 17 092 C2  12/1990  Germany.

*Primary Examiner*—Vincent Millin
*Assistant Examiner*—Dinh X. Nguyen
*Attorney, Agent, or Firm*—McGlew and Tuttle

[57] ABSTRACT

A delivery device for supplying a respirator with breathing gas includes a cylinder housing with a piston, and a drive unit for generating delivery strokes, which is connected to the piston via a piston rod. A compact design is achieved by providing the drive unit with a motor-driven hollow shaft with a spindle acting as a piston rod displaceable in it telescopically.

18 Claims, 2 Drawing Sheets

5,755,223

DELIVERY DEVICE FOR A RESPIRATOR

FIELD OF THE INVENTION

The present invention pertains to a delivery device for supplying a respirator with breathing gas, the delivery device containing a cylinder housing with a piston, and a drive unit for generating delivery strokes, which is connected to the piston via a piston rod, wherein the gas connection lines for the breathing gas to be delivered open into the inner space of the cylinder housing.

BACKGROUND OF THE INVENTION

A delivery device, with which breathing gas is pumped into the respiratory circulation of a respirator, has been known from DE 38 17 092 C2. The delivery device contains a piston-and-cylinder unit, which is placed into a housing of the respirator and is connected to a drive unit actuating the piston.

The drawback of the prior-art delivery device is that together with the drive unit, the piston-and-cylinder unit requires a relatively large space within the respirator. In the prior-art delivery device, the drive unit consists of a complicated belt drive, which is connected to the piston rod actuating the piston by means of a coupling piece. Even though accurate metering of small stroke volumes of breathing gas is possible with the prior-art delivery device, accurate metering is not needed for many applications. Thus, accurate metering of small breath stroke volumes is not necessary in the case of the artificial respiration of adults.

SUMMARY AND OBJECTS OF THE INVENTION

The primary object of the present invention is to improve a delivery means for breathing gas such that it has a compact design and can be especially easily integrated in a respirator.

This object is accomplished by the drive unit having a motor-driven hollow shaft with a spindle accommodated on it telescopically acting as the piston rod.

According to the invention, a delivery device is provided for supplying a respirator with breathing gas. The delivery device includes a cylinder housing with a piston, and a drive unit for generating delivery strokes. The drive unit is connected to the piston via a piston rod, wherein said gas connection lines for the breathing gas to be delivered open into the inner space of the cylinder housing. The drive unit has a motor-driven hollow shaft with a spindle acting as the piston rod accommodated on the shaft telescopically.

The advantage of the present invention is essentially that an especially compact unit is obtained for the volume displacement of breathing gases due to the motor-driven hollow shaft with a spindle telescopically displaceable in it. A drive unit of such a design can be connected to a piston-and-cylinder unit in an especially simple manner, because the spindle accommodated in the hollow shaft can also actuate the piston at the same time.

The motor drive is advantageously an electric motor, preferably a so-called disk armature motor, whose drive axle is designed directly as a hollow shaft. The end of the hollow shaft that is open toward the spindle is provided with a spindle nut, in which the spindle is guided.

To achieve the lowest possible wear of the spindle within the spindle nut, an elastic coupling element, with which a possible angular offset between the piston and the spindle can be compensated, is provided between the piston and the spindle.

The drive unit is advantageously arranged on a wall part fastened to the lower front side of the cylinder housing.

It is especially advantageous to fasten the cylinder housing together with the drive unit on a bracket that can be pivoted into the housing of the respirator. The housing of the respirator can thus be used especially well in a space-saving manner for accommodating the delivery means. The bracket is designed such that it is also a limiting surface of the housing of the respirator at the same time.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
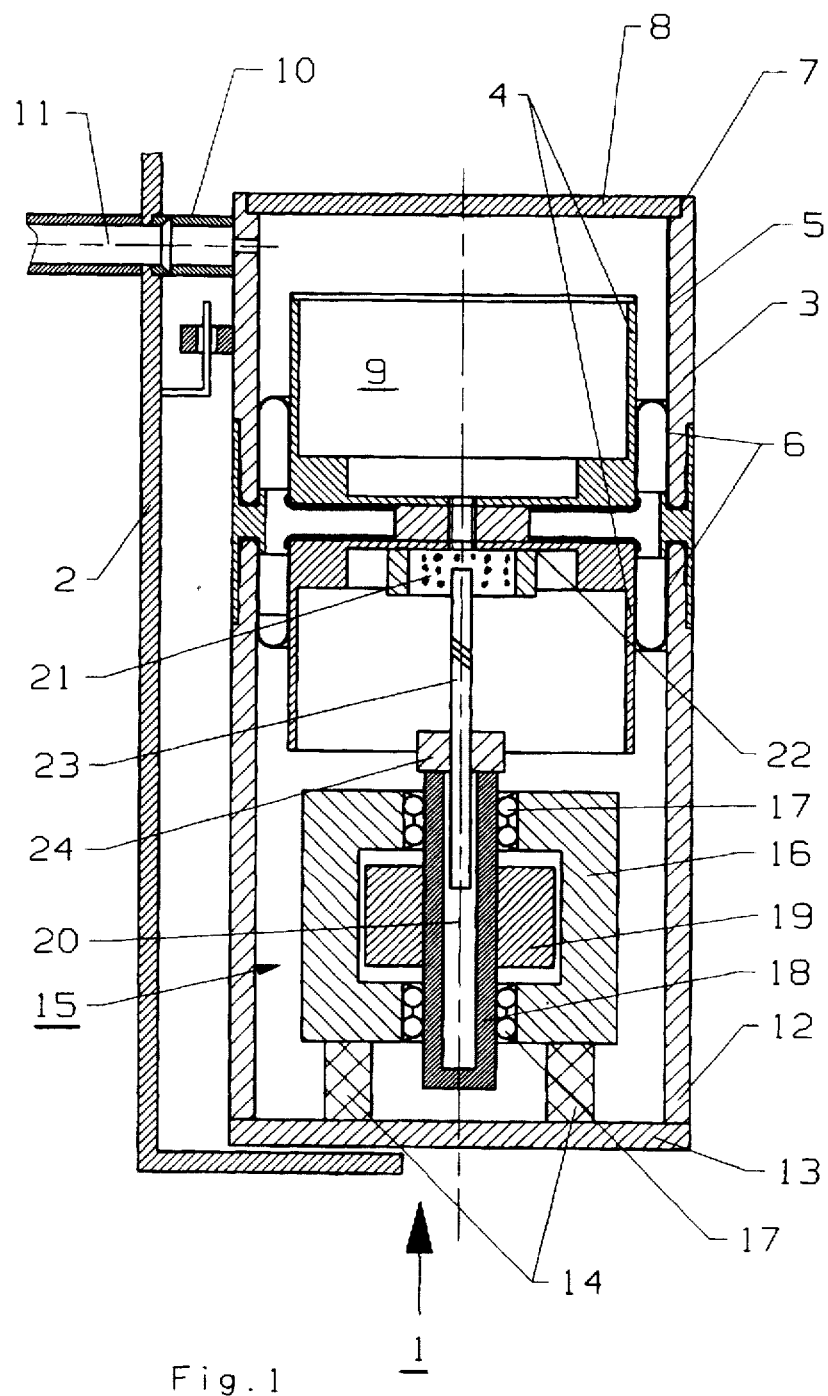
FIG. 1 is a longitudinal section of a delivery means.

Referring to the drawings in particular, FIG. 1 shows a delivery unit 1 fastened to a bracket 2 for supplying a respirator, not shown in the figure, with breathing gas. The delivery unit 1 comprises a double piston 4, which is accommodated in a cylinder housing 3 and is sealed against the cylinder wall 5 with a double rolling membrane 6. The cylinder housing 3 is closed with a plate 8 on its top front side 7. The plate 8, the double piston 4, and the cylinder wall 5 enclose a working chamber 9, in which the breathing gas to be delivered is located. The breathing gas enters a breathing system, not shown in FIG. 1, via a connecting branch 10 and a line 11. The lower front side 12 of the cylinder housing 3 is closed with a wall part 13, on which a disk armature motor 15 is fastened via an elastic mount 14. The disk armature motor 15, which is also shown as a longitudinal section, comprises a motor housing 16, a hollow shaft 18, which is rotatably mounted in the motor housing 16 via ball bearings 17, and a rotor 19 driving the hollow shaft 18. The hollow shaft 18 has an inner space 20 for accommodating a spindle 23, which is connected to a lower piston surface 22 of the double piston 4 via an elastic coupling element 21. A spindle nut 24, in which the spindle 23 is guided, is fastened at the end of the hollow shaft 18 that is open toward the spindle 23. The spindle 23 is designed as a recirculating-ball spindle. Depending on the direction of rotation, the spindle 23 is pushed telescopically out of the inner space 20 or into the inner space 20 during the rotation of the hollow shaft 18. An especially small space requirement is obtained for the drive unit 15 and consequently the delivery means 1 due to the telescopic arrangement of the spindle 23 within the hollow shaft 18.

Figure 2:
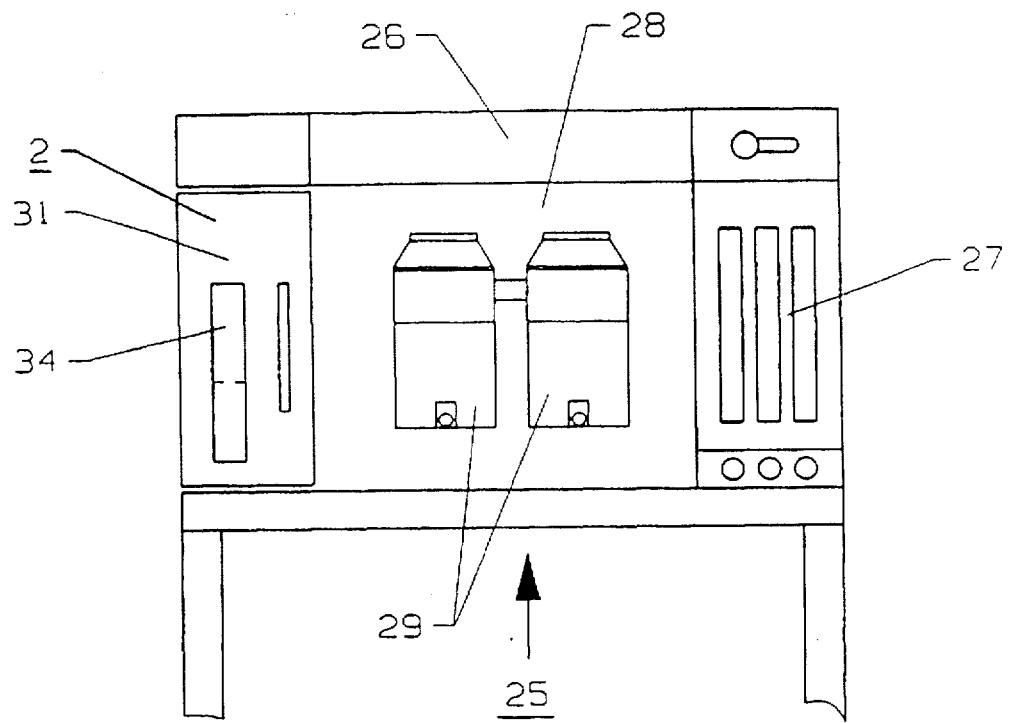
FIG. 2 is a front view of a respirator with the delivery means according to FIG. 1.

FIG. 2 shows a front view of a respirator 25 with the bracket 2 accommodating the delivery means 1. The respirator 25 has a gas-metering unit 27 in its housing 26 in the known manner, and two anesthetic-metering devices 29 are arranged on a front side 28 of the housing 26 facing the user.

Figure 3:
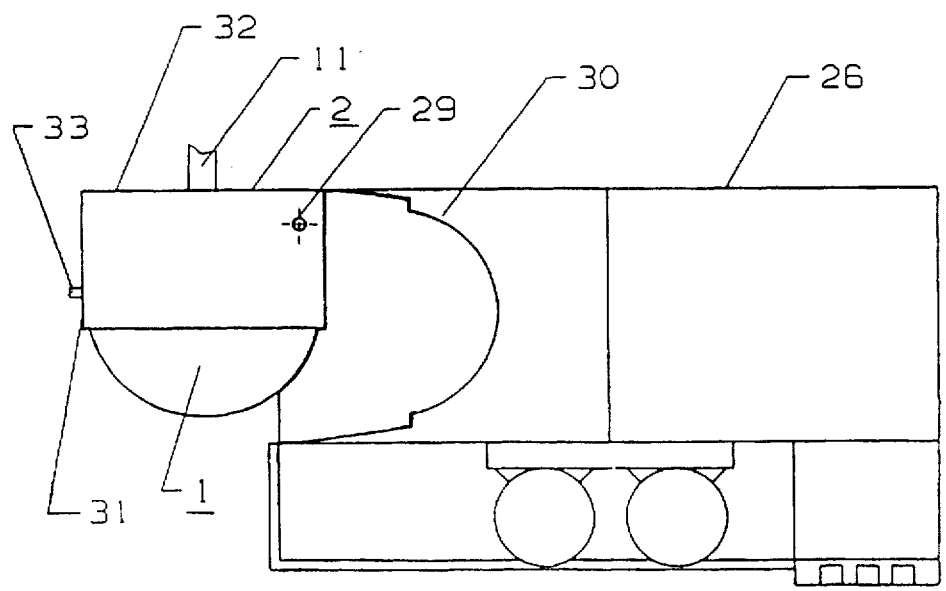
FIG. 3 is a top view of the respirator according to FIG. 2.

FIG. 3 shows a top view of the respirator according to FIG. 2, with the bracket 2 that can be pivoted out of the housing 26, with the delivery means 1 located on it. The bracket 2 is fastened to the housing 26 pivotably around a joint 29. The space required by the bracket 2 and the delivery means 1 within the housing 26 is illustrated by the area 30 in FIG. 3. The bracket 2 has two wall surfaces extending at right angles to one another, of which one operating surface 31 extends aligned with the front side 28, and a lateral surface 32 forms the lateral closure of the housing 26. A handle 33 for performing the pivoting movement, and a window 34, through which the position of the double piston 4 can be recognized, are arranged on the operating surface 31. The cylinder housing 3 has an opening, not shown in FIG. 1, for this purpose in the area of the window 34. An especially compact design of the respirator 25 is obtained due to the delivery means 1 being pivoted into the housing 26.

While a specific embodiment of the invention has been shown and described in detail to illustrate the application of the principles of the invention, it will be understood that the invention may be embodied otherwise without departing from such principles.

What is claimed is:

1. A delivery device for supplying a respirator with breathing gas, the delivery device comprising:

a substantially cylindrical housing a piston disposed in said housing;

a drive unit for generating piston delivery strokes, said drive unit being connected to said piston via a piston rod, said drive unit including a motor-driven hollow shaft with a spindle forming said piston rod, said spindle being accommodated on said hollow shaft telescopically;

gas connection lines for the breathing gas to be delivered, said gas connection lines opening into an inner space of said cylinder housing;

an elastic coupling element provided between said piston and said spindle.

2. A delivery device in accordance with claim 1, wherein said drive unit is an electric motor, with a drive axle forming said hollow shaft.

3. A delivery device in accordance with one of claim 1, wherein said drive unit is arranged on a wall part of said cylinder housing.

4. A delivery device in accordance with claim 1, wherein said drive unit together with said cylindrical housing is fastened on a bracket, said bracket being connected to a respirator housing, and said bracket is for pivoting said cylindrical housing relative to said respirator housing.

5. A delivery device in accordance with claim 4, wherein said bracket has an operating surface, and said bracket has a window for detecting the position of said piston.

6. A delivery device in accordance with claim 5, wherein said bracket has a lateral surface extending essentially at right angles to said operating surface.

7. A delivery device in accordance with claim 6, wherein said operating surface and said lateral surface are limiting surfaces of said housing of said respirator.

8. A respirator delivery device, comprising:

a housing;

a piston disposed in said housing;

a drive unit for generating piston delivery strokes, said drive unit including a motor, a hollow shaft rotationally driven by said motor and a spindle connected to said hollow shaft, said spindle moving telescopically upon rotation of said hollow shaft, said spindle being connected to said piston;

gas connection lines for the breathing gas to be delivered, said gas connection lines opening into an inner space of said cylinder housing and;

an elastic coupling element provided between said piston and said spindle.

9. A delivery device in accordance with claim 8, wherein said drive unit is an electric motor, with a drive axle forming said hollow shaft.

10. A delivery device in accordance with one of claim 8, wherein said drive unit is arranged on a wall part of said cylinder housing.

11. A delivery device in accordance with claim 8, wherein said drive unit together with said housing is fastened on a bracket, said bracket being connected to a respirator housing, and said bracket is for pivoting said cylindrical housing relative to said respirator housing.

12. A delivery device in accordance with claim 11, wherein said bracket has an operating surface, and said bracket has a window for detecting the position of said piston.

13. A delivery device in accordance with claim 12, wherein said bracket has a lateral surface extending essentially at right angles to said operating surface.

14. A delivery device in accordance with claim 13, wherein said operating surface and said lateral surface are limiting surfaces of said housing of said respirator.

15. A respirator delivery device, comprising:

a housing;

a piston disposed in said housing;

a drive unit for generating piston delivery strokes, said drive unit including a motor, a hollow shaft rotationally driven by said motor and a spindle connected to said hollow shaft, said spindle moving telescopically upon rotation of said hollow shaft, said spindle being connected to said piston, said drive unit together with said housing being fastened on a bracket, said bracket being connected to a respirator housing, said bracket for pivoting said cylindrical housing relative to said respirator housing; and gas connection lines for the breathing gas to be delivered, said gas connection lines opening into an inner space of said cylinder housing.

16. A delivery device in accordance with claim 15, wherein:

said bracket has an operating surface, and said bracket has a window for detecting the position of said piston.

17. A delivery device in accordance with claim 16, wherein:

said bracket has a lateral surface extending essentially at right angles to said operating surface.

18. A delivery device in accordance with claim 17, wherein:

said operating surface and said lateral surface are limiting surfaces of said housing of said respirator.

* * * * *